United States Patent [19]
Wissner

[11] Patent Number: 4,939,127
[45] Date of Patent: * Jul. 3, 1990

[54] ANTIHYPERTENSIVE PHOSPHATE DERIVATIVES

[75] Inventor: Allan Wissner, Ardsley, N.Y.

[73] Assignee: American Cyanamid Company, Stamford, Conn.

[ * ] Notice: The portion of the term of this patent subsequent to Oct. 27, 2004 has been disclaimed.

[21] Appl. No.: 96,910

[22] Filed: Sep. 15, 1987

Related U.S. Application Data

[63] Continuation of Ser. No. 679,789, Dec. 10, 1984.

[51] Int. Cl.[5] ........................ A61K 31/685; C07F 9/10
[52] U.S. Cl. ........................................ 514/77; 540/487; 546/22; 558/166; 558/170; 548/413
[58] Field of Search .................. 558/169, 170; 514/77; 540/487; 544/22; 548/112

[56] References Cited

U.S. PATENT DOCUMENTS 4,703,130 10/1987 Wissner .............................. 558/169

FOREIGN PATENT DOCUMENTS 0070433 1/1983 European Pat. Off. .

OTHER PUBLICATIONS

Hanahan et al., Biochemical and Biophysical Research Communications, vol. 99, No. 1, 1981, pp. 183–188.
Tence et al., Biochimie, 1981, 63, 723–727.
Tence et al., Biochimica et Biophysica Acta, 755 (1983).

*Primary Examiner*—Anton H. Sutto
*Attorney, Agent, or Firm*—Thomas S. Szatkowski

[57] ABSTRACT

Antihypertensive phosphate derivatives having the following formula are described:

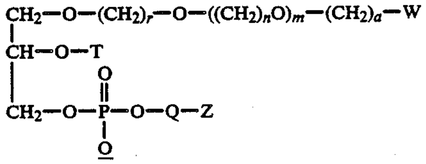

wherein W is selected from the group consisting of methyl and phenyl optionally substituted with $C_1$–$C_3$ alkyl, $C_1$–$C_3$ alkoxy and phenyl; r, n, m and a are integers such that the expression r+(n+1)m+a is also an integer and has a value of 3 to 20; r is greater than or equal to 2; n is greater than or equal to 2; m is greater than or equal to zero and a is greater than or equal to zero; T is selected from the group consisting of hydrogen and

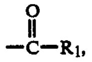

wherein $R_1$ is selected from the group consisting of hydrogen, $C_1$–$C_4$ branched or straight chain alkyl, $C_1$–$C_4$ branched or straight chain alkoxy and $C_1$–$C_4$ branched or straight chain alkylamino; Q is a bivalent radical selected from $-(CH_2)_p-$ and $-(CHR)_p-$, wherein p is an integer 2-12 and the moiety $-(CHR_p-$ represents an alkylene chain which is substituted by one or more $C_1$–$C_{10}$ alkyl groups or phenyl groups; Z is selected from the group consisting of $\pm N(R_2)_3$ and 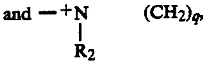

wherein $R_2$ may be the same or different and is selected fromthe group consisting of hydrogen and $C_1$–$C_4$ branched or straight chain alkyl and q is an integer from 4–7; in either the racemic or optically active forms.

14 Claims, No Drawings

ANTIHYPERTENSIVE PHOSPHATE DERIVATIVES

This is a continuation of application Ser. No. 679,789 filed Dec. 10, 1984.

BACKGROUND OF INVENTION

This invention pertains to novel phosphate derivatives, and to methods of preparation of such compounds. This invention is also concerned with compositions useful in the treatment of hypertension.

It is estimated that approximately fifteen percent (15%) or more of the adult population in the United States is hypertensive, i.e., having blood pressures greater than or equal to about 160/95 mm Hg. Of that population, approximately one-half is unaware of their hypertensive condition. An untreated hypertensive is at great risk of developing disabling or fatal left ventricular failure, myocardial infarction, cerebral hemorrhage or infarction, and renal failure at an early age. Hypertension is generally considered the most important risk factor predisposing to coronary and cerebral atherosclerosis. However, it is believed that effective medical control of hypertension will prevent or forestall all complications associated with hypertension, and will prolong the life of the hypertensive patient.

Drug therapy for hypertension includes use of diuretics, sympathetic depressants (e.g., α-blockers such as reserpine), vasodilators and finally blockers of sympathetic transmission at the neuroeffector junction (e.g., guanethidine or clonidine).

Among the vasodilators currently employed in hypertension therapy are diazoxide and sodium nitroprusside. Side effects of diazoxide therapy include nausea, vomiting, hyperglycemia and tachycardia. Side effects from sodium nitroprusside therapy include nausea, vomiting, agitation, muscular twitching and cutis anserina if blood pressure is reduced too rapidly. Minoxidil is also often used as a vasodilator in hypertension therapy. However, the side effects of minoxidil include sodium and water retention, and hirsutism. Hydralazine, a mild vasodilator, is also employed. Its side effects include headaches, tachycardia, fluid retention, aggravation of angina, gastrointestinal irritation, lupus-like syndrome, drug fever and psychosis.

Acetyl glyceryl ether phosphocholines have been recognized as having potent biological activity in platelet activation, and in vasoconstriction and vasodilation. See, e.g., U.S. Pat. No. 4,329,302, which issued on May 11, 1982 to Hanahan, et al. Such phosphocholines have been identified as both a platelet activation factor (PAF) and an antihypertensive polar renomedullary lipid (APRL). See R. L. Wykle, et al., FEBS LETTERS, 141: 29–32 (1982); M. L. Blank, et al., BIOCHEMICAL AND BIOPHYSICAL RESEARCH COMMUNICATIONS, 90: 1194–1200 (1979). Antihypertensive phosphocholines do not occur as pre-formed components in the body; rather, such phosphocholines are synthesized by certain cells. See J. Benveniste, et al., INT. ARCHS. ALLERGY APPL. IMMUNN., 66 (Supp. 1): 121–126 (1981); E. E. Muirhead, HYPERTENSION, 2: 444–464 (1980). APRL has been described as being accountable in great measure for the endocrine-type antihypertensive action exerted by the renal medullary and the renomedullary interstitial cells. M. L. Blank, et al., ID.

BRIEF SUMMARY OF THE INVENTION

The phosphate derivatives of the present invention have the formula:

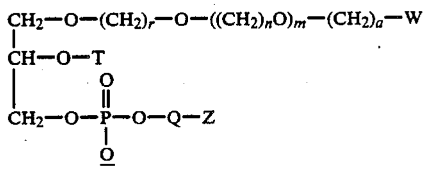

wherein W is selected from the group consisting of methyl and phenyl optionally substituted with $C_1$-$C_3$ alkyl, $C_1$-$C_3$ alkoxy and phenyl; r, n, m and a are integers such that the expression $r+(n+1)m+a$ is also an integer and has a value of 3 to 20; r is greater than or equal to 2; n is greater than or equal to 2; m is greater than or equal to zero and a is greater than or equal to zero; T is selected from the group consisting of hydrogen and

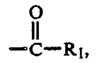

wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino; Q is a bivalent radical selected from $-(CH_2)_p-$ and $-(CHR)_p-$, wherein p is an integer 2-12 and the moiety $-(CHR)_p-$ represents an alkylene chain which is substituted by one or more $C_1$-$C_{10}$ alkyl groups or phenyl groups; Z is selected from the group consisting of $\pm N(R_2)_3$ and and 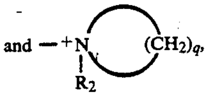

wherein $R_2$ may be the same or different and is selected from the group consisting of hydrogen and $C_1$-$C_4$ branched or straight chain alkyl and q is an integer from 4–7; in either the racemic or optically active forms.

DETAILED DESCRIPTION OF THE INVENTION

In order to prepare the compounds of this invention certain tosylates of formula 4 and formula 13 are needed. These are prepared as outlined hereinbelow in Flowsheets A-D wherein W, r, n, m and a are as defined hereinabove and W' is a phenyl group optionally substituted with $C_1$-$C_3$ alkyl, $C_1$-$C_3$ alkoxy and phenyl and wherein TSO represents a tosylate group:

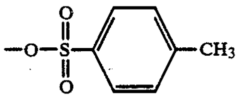

and wherein J is a halogen atom (chlorine, bromine or iodine).

According to the reactions shown in Flowsheet A, a diol of formula 1 is reacted with one equivalent of an alkyl halide 2 using sodium hydride in an inert solvent such as tetrahydrofuran or dimethylformamide or mixtures of both to give the monoalkylated compound 3. Compound 3 can be readily separated from the unreacted 1 and the dialkylated side product by fractional distillation or if necessary, by liquid or gas chromatographic techniques well known in the art. The alcohol 3 is then converted to the tosylate 4 using p-toluenesulfonyl chloride in pyridine. In those cases where m is zero, compounds of formula 4a are produced:

$$TSO-(CH_2)_r-O-(CH_2)_a-W \quad 4a$$

-continued

FLOWSHEET A

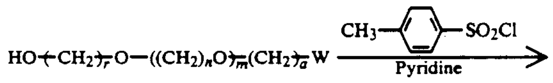

3

$$TSO-(CH_2)_r-O-((CH_2)_nO)_m-(CH_2)_a-W$$

4

FLOWSHEET B $$CH_2{=}CH-(CH_2)_{r-2}-J + HO-((CH_2)_nO)_m-(CH_2)_a-W \xrightarrow[DMF]{NaH}$$

5 6

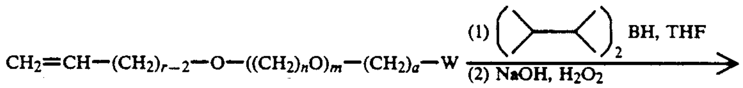

7

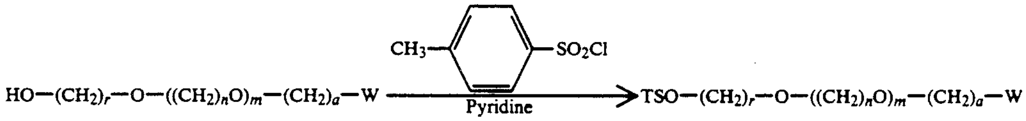

3 4

The tosylates of structure 4 can also be prepared as outlined hereinbelow in Flowsheet B. Alkylation of alcohol 6 with an alkyl halide 5 containing a terminal double bond with a hydride base such as sodium hydride in an inert solvent such as dimethylformamide gives 7. Hydroboration of 7 with borane or a substituted borane in an inert solvent such as tetrahydrofuran gives, after oxidation with hydrogen peroxide and base, the alcohol 3. Alcohol 3 is then converted to the tosylate as described above. This sequence can also be applied in those cases where m is zero, resulting in compound 4a.

According to Flowsheet C, alkylation of a phenol or substituted phenol 9 with an alkyl halide 8 under phase transfer conditions gives the alcohol 10 which is converted to the tosylate 11 by the usual conditions.

Compounds of structure 4 can also be prepared as described hereinbelow in Flowsheet D. The reaction of alcohol 13 with an alkyl halide 12, which has a terminal tetrahydropyranyloxy (THP) group, using sodium hydride in an inert solvent gives the compound 14. The tetrahydropyranyloxy group of 14 is readily removed by hydrolysis under acidic conditions such as dilute hydrochloric acid in a solvent mixture such as tetrahydrofuran-water to give alcohol 3 which is converted as described above to tosylate 4. As before, this procedure can be used to prepare compounds 4a in those cases where m is zero.

FLOWSHEET A $$HO-(CH_2)_r-O-((CH_2)_nO)_{m-1}-(CH_2)_n-OH +$$

1

$$J-(CH_2)_a-W \xrightarrow[THF-DMF]{NaH}$$

2

FLOWSHEET C $$HO-(CH_2)_r-J + HO-W' \xrightarrow[H_2O-THF]{NaOH,\ (C_8H_{17})_3NCH_3{}^+Cl^-}$$

8 9

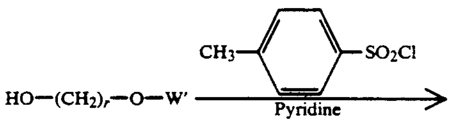

10

$$TSO-(CH_2)_r-O-W'$$

11

FLOWSHEET D $$THP-O-(CH_2)_r-J +$$

12

$$HO-((CH_2)_nO)_m-(CH_2)_a-W \xrightarrow[DMF]{NaH}$$

13

$$THP-O-(CH_2)_r-O-((CH_2)_nO)_m-(CH_2)_a-W \xrightarrow{H_3O^+}$$

14

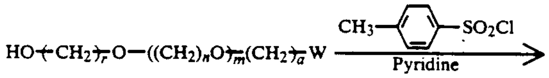

3

-continued

FLOWSHEET D $TSO-(CH_2)_r-O-((CH_2)_nO)_m-(CH_2)_a-W$

4

Compounds of this invention represented by structure 25 are prepared as outlined hereinbelow in Flowsheet E, wherein r, n, m, a, W, T, Q, Z, $R_1$, p, q and $R_2$ are as defined hereinabove. These reactions are also applicable for the preparation of compound 25a (compounds where m=zero).

Alkylation of solketal 15 with tosylate 4 using sodium hydride in an inert solvent such as dimethylformamide, followed by removal of the diol protecting group using p-toluenesulfonic acid or an acidic ion exchange resin in methanol gives the diol 16. The diol 16 is reacted with a reagent which only functionalizes the primary hydroxy group; one such reagent is p-anisylchlorodiphenylmethane in pyridine or mixed solvent containing pyridine; this provides the monoprotected compound 17. This is converted to the compound 18 by alkylation with benzyl bromide using sodium hydride in an inert solvent followed by treatment with methanol and an acidic catalyst such as p-toluenesulfonic acid or an acidic anion exchange resin to remove the p-methoxy trityl protecting group.

The reaction of 18 with the phosphorous reagents 19a or 19b in an inert solvent such as carbon tetrachloride with a base such as triethylamine gives, after hydrolysis in a buffer such as aqueous sodium acetate, the phosphate compound 20. The reaction of 20 with amines 21a or 21b in a refluxing inert solvent or in a bomb at elevated temperature affords compound 22. Suitable alkyl amines capable of use in the present process are shown in Table III, following Example 25 herein. The benzyl protecting group of 22 is removed by hydrogenolysis to give the alcohol 23.

The compounds represented by the formula 23 can be converted to compounds 25 of this invention wherein $R_1$ is an alkyl group by the reaction of 23 with an anhydride 24a in the presence of a base catalyst such as triethylamine in an inert solvent such as chloroform.

The compounds represented by the formula 23 can be converted to compounds 25 of this invention wherein $R_1$ is a $C_1$–$C_4$ alkoxy group by the reaction of 23 with a pyrocarbonate 24c in the absence of solvent at elevated temperature (about 50°–150° C.).

The compounds represented by the formula 23 can be converted to compounds 25 of this invention wherein $R_1$ is hydrogen by the reaction of 23 with about 97% formic acid at room temperature for about 3 to 7 days.

The compounds represented by the formula 23 can be converted to compounds 25 of this invention wherein $R_1$ is a $C_1$–$C_4$ alkylamino group by treatment of 23 with an isocyanate 24b in and inert solvent such as toluene at about 25°–100° C. for about 1–7 days.

Since compound 15 is available in either the optically active R or S forms, or in the optically inactive racemic form, the compounds of this invention represented by the formula 25 and 25a can be prepared in the corresponding optically active R and S configurations or in the optically inactive racemic form by choosing the proper starting material [E. Baer, BIOCHEMICAL PREP., 2: 31 (1952); M. E. Jung and T. J. Shaw, J. AMER. CHEM. SOC., 102: 6304 (1980)].

FLOWSHEET E

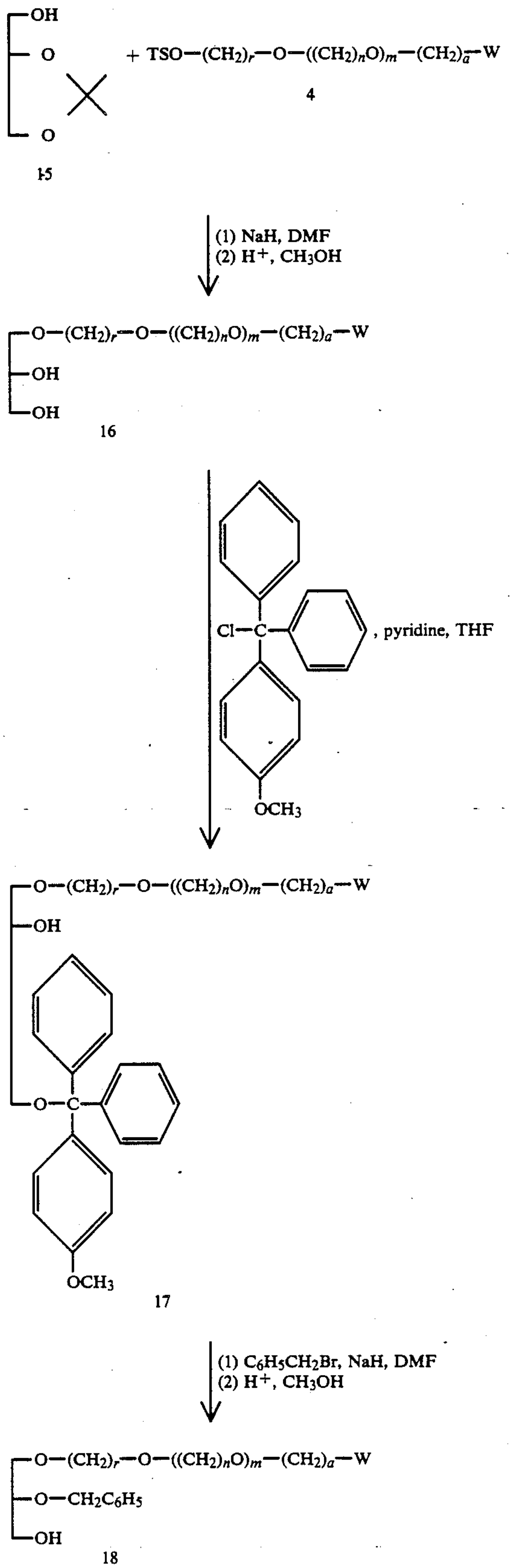

-continued

FLOWSHEET E

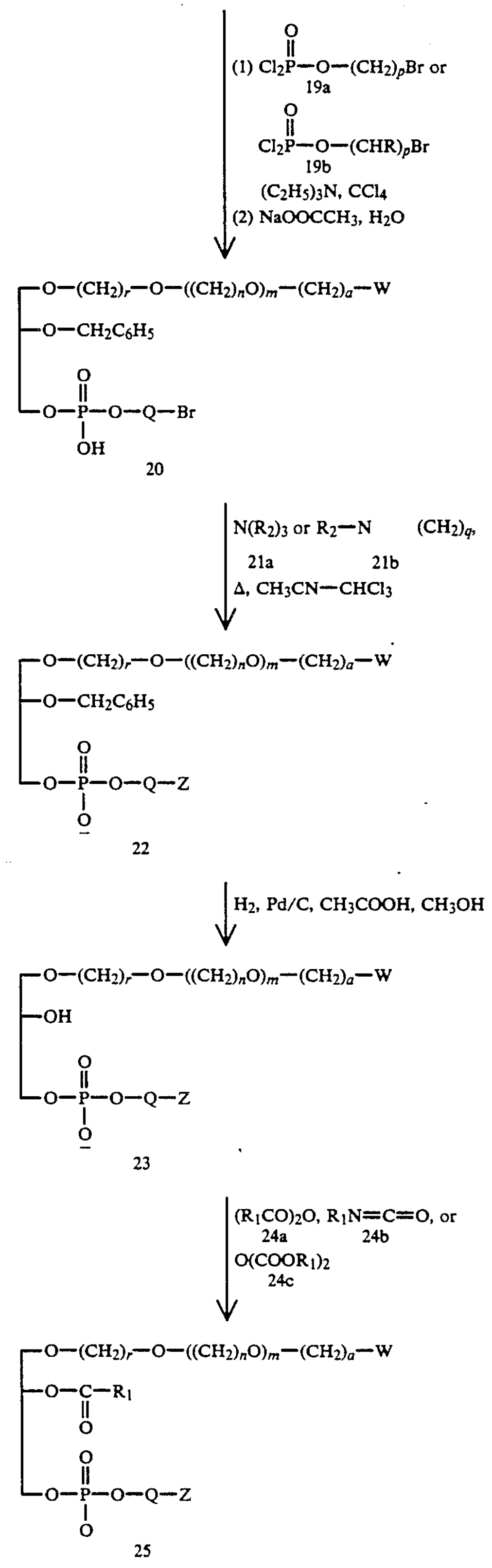

when m = 0

-continued

FLOWSHEET E

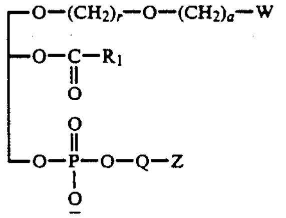

25a

The methods for the preparation of the phosphorous reagents 19a and 19b, used to prepare the compounds of this invention, are described in a copending application for U.S. Pat., Ser. No. 457,097, filed Jan. 10, 1983 which application issued as U.S. Pat. No. 4,640,913 on Feb. 3, 1987. which is incorporated herein by reference, and in the following prior art references: E. Baer and N. Ž. Stanacey, J. BIOL. CHEM., 240, 3754 (1965); A. Eberhard and F. H. Westheimer, J. AMER. CHEM. SOC., 37, 253 (1965). By using such procedures, the bromo alcohols of Table I are converted to the indicated phosphorodichlorodates.

TABLE I

| Bromo Alcohol | Phosphorodichlorodate |
|---|---|
| 2-bromoethanol | 2-bromoethyl phosphorodichlorodate |
| 3-bromopropanol | 3-bromopropyl phosphorodichlorodate |
| 2-bromopropanol | 2-bromopropyl phosphorodichlorodate |
| 2-bromo-1-methylethanol | 2-bromo-1-methylethyl phosphorodichlorodate |
| 4-bromobutanol | 4-bromobutyl phosphorodichlorodate |
| 5-bromopentanol | 5-bromopentyl phosphorodichlorodate |
| 3-bromo-3-methylpropanol | 3-bromo-3-methylpropyl phosphorodichlorodate |
| 3-bromo-2-methylpropanol | 3-bromo-2-methylpropyl phosphorodichlorodate |
| 3-bromo-1-methylpropanol | 3-bromo-1-methylpropyl phosphorodichlorodate |
| 2-bromo-2-phenylethanol | 2-bromo-2-phenylethyl phosphorodichlorodate |
| 3-bromo-2-phenylpropanol | 3-bromo-2-phenylpropyl phosphorodichlorodate |

The compounds of the present invention are active as hypotensive agents as evidenced by their activity in the following test, the results of which are shown in Table II.

Under ether anesthesia, Weeks type cannulas (Peterson Technics) were surgically implanted in the abdominal aorta and vena cava of spontaneously hypertensive rats (Taconic Farms, Germantown, NY) and passed subcutaneously to the back of the neck where they were exteriorized. The cannulas were filled with saline, plugged and the rats returned to single cages where they were allowed food and water ad libitum.

At least three days following implantation of the cannulas, the rats were weighed and placed in Broome style restraining cages. The plug was removed from the aortic catheter which was connected to an arterial pressure transducer (Statham P23ID) using PE 100 polyethylene tubing and a stepdown connector fabricated from stainless steel hypodermic tubing. Mean arterial blood pressure was obtained by electrical damping of the pulse pressure channel. Heart rate was obtained from a tachograph triggered by the pulse pressure channel. All parameters were monitored on a Grass physiological recorder (Model 7).

The plug was removed from the vena cava catheter and a PE 20 polyethylene tubing extension was added using a piece of stainless steel hypodermic tubing. The other end was terminated with a 27G needle and one ml syringe.

All drugs were dissolved in saline or a mixture of ethanol and saline (25:75 V:V) such that the volume injected intravenously was 0.1 ml/100 g body weight. All drugs were flushed in with 0.2 ml saline. Blood pressure was continually monitored both before and after introduction of the test compound.

TABLE II

| Compound | Dose (μg/kg) | No. of Rats | Peak Δ Mean Arterial Blood Pressure (mm, Hg) |
|---|---|---|---|
| 7-(acetyloxy)-4-hydroxy-N,N,N-trimethyl-3,5,9,12,-15-pentaoxa-4-phosphapentacosan-1-aminium, 4-oxide hydroxide, inner salt | 1 | 4 | −11.8 |
| | 3 | 4 | −14.0 |
| | 10 | 4 | −37.2 |
| | 30 | 4 | −71.9 |
| | 100 | 4 | −89.3 |
| 7-(acetyloxy)-4-hydroxy-N,N,N-trimethyl-3,5,9,18,-21,24-hexaoxa-4-phospha-pentacosan-1-aminium, 4-oxide, hydroxide, inner salt | 3 | 4 | −8.9 |
| | 10 | 4 | −25.0 |
| | 30 | 3 | −34.8 |
| | 100 | 3 | −46.5 |
| | 300 | 3 | −66.6 |
| | 1000 | 3 | −87.1 |
| 7-(acetyloxy)-17-([1,1'-biphenyl]-4-yloxy)-4-hydroxy-N,N,N-trimethyl-3,5,9-trioxa-4-phospha-heptadecan-1-aminium, 4-oxide, hydroxide, inner salt | 0.3 | 5 | −9.1 |
| | 1 | 5 | −30.4 |
| | 3 | 5 | −65.2 |

When the compounds are employed for the above utility, they may be combined with one or more pharmaceutically acceptable carriers, e.g., solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05% up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.005 mg to about 100 mg/kg of animal body weight, preferably given in divided doses two to four times a day, or in sustained release form. For most large mammals the total daily dosage is from about 500 μg to about 5,000 mg preferably from about 350 μg to 3,500 mg. Dosage forms suitable for internal use comprise from about 25 μg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compound is preferred.

These active compounds may also be administered parenterally or intraperitoneally. Solutions or suspensions or these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations should contain a preservative to prevent the growth of microorganisms.

The pharmaceutical forms suitable for injection use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In addition to the above utility, some of the compounds of this invention (such as 23 of flowsheet E) are useful for the preparation of other compounds of this invention.

The invention will be more fully described in conjunction with the following specific examples which are not to be construed as limiting the scope of the invention. In addition, other applicable procedures are described in the prior art and in copending application, Ser. No. 457,907 filed Jan. 10, 1983.

EXAMPLE 1

2-[2-Dodecyloxy)ethoxy]ethanol

To a suspension of 52.06 g. of hexane washed 50% sodium hydride in 500 ml of diemthylformamide was added dropwise, with stirring over 1.5 hours, 196.71 g of diethylene glycol in 300 ml of tetrahydrofuran. This mixture was stirred an additional ½ hour, then 200 g of n-decyl bromide was added over 10 minutes. The mixture was stirred 1.5 hours to obtain a solution, then diluted with water and extracted with hexane. The hexane extract was washed with water and brine, then dried and the solvent removed. The residue was distilled in a Kugelrohr apparatus. The lower boiling material was removed at 110°-115° C., 0.35 mm and the desired compound collected at 160°-165° C., 0.1 mm, giving 97 g as a colorless liquid.

EXAMPLE 2

8-[2-(2-Methoxyethoxy)ethoxy]-1-octene

To a stirred solution of 32.63 g of hexane washed 50% sodium hydride in 300 ml of dimethylformamide, under argon, was added 100 g of 8-bromo-1-octene followed by the dropwise addition of 27.2 g of (2-methoxyethoxy)ethanol in 100 ml of dimethylformamide over a period of one hour. After stirring for 3 hours the mixture was poured into water and extracted with ether. The ether extract was dried, the solvent removed and the residue distilled on a Kugelrohr at 80°-90° C., 0.2 mm, giving the desired compound as a colorless liquid.

EXAMPLE 3

8-[2-(2-Methoxyethoxy)ethoxy]-1-octanol

To 564.3 ml of 1M diborane in tetrahydrofuran was added, at 0° C. under argon with stirring, 79.16 g of 2-methyl-2-butene. After stirring for ½ hour, 65 g of 8-[2-(2-methoxyethoxy]-2-octene was added. This mixture was stirred one hour at room temperature, then 700 ml of 1M diborane in tetrahydrofuran was added over a period of 1.5 hours. The mixture was then stirred 2 hours, then water was added and about ⅔ of the tetrahydrofuran removed. The remainder was stirred in an ice bath as 150 ml of 3N sodium hydroxide was added, followed by the slow addition of 150 ml of 30% hydrogen peroxide. After stirring ½ hour the mixture was extracted with ether. The ether extract was washed in succession with saturated aqueous sodium chloride, saturated aqueous sodium bisulfite, saturated aqueous sodium chloride, then dried and the solvent removed. The residue was distilled on a Kugelrohr apparatus. The fraction boiling at 90°-110° C., 0.2 mm was discarded. The fraction boiling at 160°-180° C., 0.2 mm was collected giving 41.3 g of the desired compound as a clear liquid.

EXAMPLE 4

8-([1,1'-Biphenyl]-4-yloxy)-1-octanol

A mixture of 37.8 g of 8-bromo-1-octanol, 30.77 g of 4-phenylphenol, 8.31 g of sodium hydroxide and 34 g of N-methyl-N,N-diocyl-1-octanaminium chloride in 100 ml of water and 175 ml of tetrahydrofuran was refluxed for 17 hours. The tetrahydrofuran was removed and the residue extracted with warm chloroform. The chloroform extract was washed with water, dried and the solvent removed. The residue was recrystallized from methanol, giving 35.26 g of the desired compound as a white solid, mp 101°-103° C.

EXAMPLE 5

1-[[2-[2-(Decyloxy)ethoxy]ethyl]sulfonyl]-4-methylbenzene

A mixture of 116 g of 2-[2-(decyloxy)ethoxy]-ethanol, 98.73 g of tosyl chloride and 600 ml of pyridine was stored in a chill room overnight, then poured into water and extracted with ether. The ether extract was washed successively with water, dilute hydrochloric acid and dilute aqueous sodium bicarbonate, dried and the ether removed, giving 146.3 g of the desired compound as an oil.

EXAMPLE 6

1-[[8-[2-(2-Methoxyethoxy)ethoxy]octyl]sulfonyl]-4-methylbenzene

A mixture of 40 g of 8-[2-(2-methoxyethoxy)ethoxy]-1-octanol, 35.31 g of tosyl chloride and 200 ml of pyridine was stored in a chill room overnight, then poured into water and extracted with ether. The ether extract was washed successively with water, dilute hydrochloric acid and saturated aqueous sodium bisulfite, dried and the solvent removed, giving the desired compound as an oil which was used without further purification in Example 8.

EXAMPLE 7

4-[[8-[(4-Methylphenyl)sulfonyl]octyl]oxy]-1,1-biphenyl

A mixture of 33.26 g of 8-([1,1'-biphenyl]-4-yloxy)-1-octanol, 23.37 g of tosyl chloride and 200 ml of pyridine was allowed to stand in a refrigerator overnight. Then water was added, the solid collected, washed with water and dissolved in chloroform. This solution was washed with dilute hydrochloric acid then saturated aqueous sodium bicarbonate, dried and the solvent removed, giving the desired compound as a white solid.

EXAMPLE 8

3-[2-[2-(Decyloxy)ethoxy]ethoxy]-1,2-propanediol

To a suspension of 20.98 g of hexane washed 50% sodium hydride in 300 ml of dimethylformamide was added, dropwise over one hour, 72.25 g of solketal. This mixture was cooled in an ice bath under argon and a solution of 146 g of 1-[[2-[2-(decyloxy)ethoxy]ethyl]sulfonyl]-4-methylbenzene in 100 ml of dimethylformamide was added over ½ hour. This mixture was stirred under argon for 3 hours at room temperature, then poured into water and extracted with ether. The ether extract was dried and the solvent removed. A mixture of 600 ml of methanol, 100 ml of water and 4.5 ml of concentrated sulfuric acid was added and the solution was heated on a steam bath for 40 minutes. The methanol was removed and the residue mixed with ether. The ether layer was washed with water, then dilute aqueous sodium bicarbonate, dried and the solvent removed. The residue was distilled on a Kugelrohr apparatus. The fraction boiling at 150°-170° C., 0.05 mm was discarded. The fraction boiling at 220°-225° C., 0.05 mm gave 99 g of the desired compound as a colorless oil.

EXAMPLE 9

2,5,8,17-Tetraoxaeicosane-19,20-diol

To a suspension of 9.01 g of unwashed 50% sodium hydride in 100 ml of dimethylformamide was added, dropwise over one hour, 22.06 g of solketal. After cooling in an ice bath a solution of 42 g of 1-[[8-[2-(2-methoxyethoxy)ethoxy]octyl]sulfonyl]-4-methylbenzene in 25 ml of dimethylformamide was added. This mixture was stirred for 2 days, then water was added and the mixture extracted with ether. The ether extract was dried and the solvent removed. The residue was refluxed for one hour in a mixture of 175 ml of methanol, 25 ml of water and 1.25 ml of concentrated sulfuric acid. The methanol was removed, saturated aqueous sodium chloride added and the mixture extracted with ethyl acetate. The organic extract was dried, the solvent removed and the residue purified by HPLC, eluting with ethyl acetate, giving 14.7 g of the desired compound as an oil.

EXAMPLE 10

3-[[8-([1,1'-Biphenyl]-4-yloxy)octyl]oxy]-1,2-propanediol

To a stirred suspension of 6.56 g of hexane washed 50% sodium hydride in 100 ml of dimethylformamide was added, dropwise over 30 minutes, a solution of 18.08 g of solketal in 75 ml of dimethylformamide. After stirring for 15 minutes, 50 g of 4-[[8-[(4-methylphenyl)-sulfonyl]octyl]oxy]-1,1-biphenyl was added followed by 50 ml of tetrahydrofuran. This mixture was stirred 2 hours, then water was added and the mixture extracted with ether. The ether extract was evaporated and the residue refluxed for 40 minutes in a mixture of 200 ml of methanol, 30 ml of water and 1.5 ml of concentrated sulfuric acid. The methanol was removed, the residue dissolved in chloroform, washed with water, dried and the solvent removed. The residue was recrystallized from methanol, giving 32.7 g of the desired compound as an off-white solid, mp 94°-96° C.

EXAMPLE 11

1-[2-[2-(Decyloxy)ethoxy]ethoxy]-3-[(4-methoxy-phenyl)diphenylmethoxy]-2-propanol A mixture of 50 g of 3-[2-[2-(decyloxy)ethoxy]ethoxy]-1,2-propanediol, 53 g of p-methoxy trityl chloride, 20 ml of pyridine and 100 ml of tetrahydrofuran was allowed to stand overnight, then poured into water and extracted with ether. The ether extract was washed with water, dried and the solvent removed, giving 93 g of the desired compound as a yellow oil, which was used without further purification in Example 14.

EXAMPLE 12

20-[(4-Methoxyphenyl)diphenylmethoxy]2,5,8,17-tetraoxaeicosan-19-ol

A mixture of 13.7 g of 2,5,8,17-tetraoxaeicosane-19,20-diol, 14.43 g of p-methoxy trityl chloride, 10 ml of pyridine and 40 ml of tetrahydrofuran was allowed to stand overnight, then poured into water and extracted with ether. The ether extract was washed with water, dried and the solvent removed. The desired compound was an oil which was used without additional purification in Example 15.

EXAMPLE 13

1-[[8-([1,1'-Biphenyl]-4-yloxy)octyl]oxy]-3-[(4-methoxyphenyl)diphenylmethoxy]-2-propanol A mixture of 30 g of 3-[[8-([1,1'-biphenyl]-4-yloxy)octyl]oxy]1,2-propanediol, 26.11 g of p-methoxy trityl chloride, 20 ml of pyridine and 100 ml of tetrahydrofuran was stirred overnight, then poured into water and extracted with ether. The ether extract was washed with water, then brine, dried and the solvent removed giving the dsired compound as an oil which was used without additional purification in Example 16.

EXAMPLE 14

3-[2-[2-(Decyloxy)ethoxy]ethoxy]-2-(phenylmethoxy)-1-propanol

To a stirred solution of 9.36 g of hexane washed 50% sodium hydride and 37.36 g of benzyl bromide in 150 ml of dimethylformamide, under argon, was added dropwise a solution of 92.49 g of 1-[2-[2-(decyloxy)ethoxy]ethoxy]-3-[(4-methoxphenyl)diphenylmethoxy]-2-propanol in 200 ml of dimethylformamide over one hour. After stirring an additional one hour, water was added and the mixture was extracted with ether. The ether extract was dried and the solvent removed. The residue was stirred in 500 ml of warm methanol containing 40 g of a strongly acidic ion exchange resin for one hour and then filtered. The solvent was removed from the filtrate and the residue purified by HPLC, eluting with hexane:ethyl acetate (7:4), giving 27.83 g of the desired compound as a colorless oil.

EXAMPLE 15

19-(Phenylmethoxy)-2,5,8,17-tetraoxaeicosan-20-ol

To a stirred suspension of 3.26 g of unwashed 50% sodium hydride and 10.9 g of benzyl bromide in 40 ml of dimethylformamide, under argon, was added a solution of 27.14 g of 20-[(4-methoxyphenyl)diphenylmethoxy]-2,5,8,17-tetraoxaeicosan-19-ol in 50 ml of dimethylformamide over ½ hour. This mixture was stirred overnight, water was then added and the mixture extracted with ether. The ether extract was washed with water, dried and the solvent removed. The residue was dissolved in hot methanol and stirred with 10 g of a strongly acidic ion exchange resin. This mixture was filtered and the solvent removed. The residue was purified by HPLC, eluting with hexane:ethyl acetate (65:35) giving the desired compound as 12.9 g of a light yellow oil.

EXAMPLE 16

3-[[8-(]1,1'-Biphenyl]-4-yloxy)octyl]oxy]-2-(phenylmethoxy)-1-propanol

To a stirred suspension of 4.83 g of hexane washed 50% sodium hydride and 15.15 g of benzyl bromide in 125 ml of dimethylformamide, under argon was added dropwise over one hour a solution of 51.93 g of 1-[[8-([1,1'-biphenyl]-4-yloxy)octyl]oxy]-3-[(4-methoxy-phenyl)diphenylmethoxy]-2-propanol in 75 ml of tetrahydrofuran. The mixture was stirred overnight, water was slowly added and the mixture extracted with ether. The ether extract was dried and the solvent removed. The residue was dissolved in a mixture of 200 ml of methanol and 50 ml of chloroform with heating to boiling. A 20 g of a strongly acidic ion exchange resin was added and the mixture was stirred 1.5 hours, then filtered and the solvent removed. The residual oil was purified by HPLC, eluting with ethyl acetate:hexane (1:4) and the residue recrystallized from hexane, giving 25.42 g of the desired compound, mp 48°-50° C.

EXAMPLE 17

4-Hydroxy-N,N,N-trimethyl-7-(phenylmethoxy)-3,5,9,12,15-pentaoxa-4-phosphapentacosan-1-aminium, 4-oxide, hydroxide, inner salt A mixture of 14 g of 3-[2-[12-(decyloxy)ethoxy]ethoxy]-2-(phenylmethoxy)-1-propanol, 12.37 g of 2-bromoethyl phosphorodichlorodate and 5.18 g of triethylamine in 170 ml of carbon tetrachloride was stirred for 1.5 hours, then filtered and the solvent removed. The residue was stirred for 2 hours in a mixture of 400 ml of 0.5M aqueous sodium acetate and 400 ml of tetrahydrofuran. The tetrahydrofuran was removed, the residue acidified and extracted with ether. The ether extract was dried, the solvent removed and the residue refluxed for 2.75 hours in a mixture of 200 ml of acetonitrile, 180 ml of chloroform and 100 g of trimethylamine.

The solvent was removed and the residue stirred for 40 minutes in a mixture of 8 g of a weak basic ion exchange resin, 2 g of silver carbonate and 100 ml of methanol. The solvent was removed and the residue chromatographed on silica gel, eluting first with chloroform:methanol (7:3) to remove higher Rf impurities and then with chloroform:methanol:water (70:30:5), giving 10.64 g of the desired compound as a colorless oil.

EXAMPLE 18

22-Hydroxy-N,N,N-trimethyl-19-(phenylmethoxy)-2,5,8,17,21,23-hexaoxa-22-phosphapentacosan-25-aminium, 22-oxide, hydroxide, inner salt A mixture of 11 g of 19-(phenylmethoxy)-2,5,8,17-tetraoxaeicosan-20-ol, 9.67 g of 2-bromoethyl phosphorodichlorodate and 4.05 g of triethylamine in 125 ml of carbon tetrachloride was stirred for 1.5 hours and then filtered. The solvent was removed and the residue stirred for 3 hours in a mixture of 300 ml of 0.5M aqueous sodium acetate and 300 ml of tetrahydrofuran. The tetrahydrofuran was removed and the residue acidified with hydrochloric acid then extracted with ether. The ether extract was dried and the solvent removed. The residue was refluxed for 3 hours in a mixture of 200 ml of acetonitrile, 180 ml of chloroform and 100 g of trimethylamine. The solvent was removed and the residue stirred for 1.5 hours in a mixture of 2 g of silver carbonate, 8 g of a weak basic ion exchange resin and 150 ml of methanol, then filtered and the solvent removed. This residue was chromatographed on silica gel, eluting first with chloroform-methanol (7:3) to remove higher Rf impurities and then with chloroform:methanol:water (70:30:5), giving 8.89 g of the desired product as a colorless oil.

EXAMPLE 19

17-([1,1'-Biphenyl]-4-yloxy)-4-hydroxy-N,N,N-trimethyl-7-(phenylmethoxy)-3,5,9-trioxa-4-phosphaheptadecan-1-aminium, 4-oxide, hydroxide, inner salt A mixture of 11 g of 3-[[8-([1,1'-biphenyl]-4-yloxy)octyl]oxy]-2-(phenylmethoxy)-1-propanol, 8.63 of 2-bromoethyl phosphorodichlorodate and 3.61 g of triethylamine in 125 ml of carbon tetrachloride was stirred for 1.5 hours, then filtered and the solvent removed. The residue was stirred for 2 hours in a mixture of 300 ml of 0.5M aqueous sodium acetate and 300 ml of tetrahydrofuran. The tetrahydrofuran was removed and the residue acidified with hydrochloric acid, then extracted with ether. The ether extract was dried, the solvent removed and the residue stirred for 3 hours at reflux in a mixture of 200 ml of acetonitrile, 180 ml of chloroform and 100 g of trimethylamine. The solvent was removed and this residue stirred for 1.5 hours in a mixture of 8 g of weak basic ion exchange resin, 2 g of silver carbonate and 200 ml of methanol. This mixture was filtered, the solvent removed and the residue chromatographed on 350 ml of silica gel eluting first with chloroform:methanol (7:3) to remove the higher Rf impurities, then with chloroform:methanol:water (70:30:5) giving 11.79 g of the desired compound as an oil.

EXAMPLE 20

4,7-Dihydroxy-N,N,N-trimethyl-3,5,9,12,15-pentaoxa-4-phosphapentacosan-1-aminium, 4-oxide, hydroxide, inner salt A mixture of 9.6 g of 4-hydroxy-N,N,N-trimethyl-7-(phenylmethoxy)-3,5,9,12,15-pentaoxa-4-phosphaheptacosan-1-aminium, 4-oxide, hydroxide, inner salt, 1.0 g of palladium on carbon, 60 ml of glacial acetic acid and 60 ml of methanol was hydrogenated for 3 hours in a Parr apparatus. The mixture was filtered, the solvents removed, toluene added and removed and then ether added. The ether was decanted from the precipitated oil which was then dried in vacuo, giving 7.7 g of the desired compound as a colorless oil.

EXAMPLE 21

19,22-Dihydroxy-N,N,N-trimethyl-2,5,8,17,21,23-hexaoxa-22-phosphapentacosan-25-aminium, 22-oxide, hydroxide, inner salt A mixture of 7.9 g of 22-hydroxy-N,N,N-trimethyl-19-(phenylmethoxy)-2,5,8,17,21,23-hexaoxa-22-phosphaheptacosan-25-aminium, 22-oxide, hydroxide, inner salt, 0.75 g of palladium on carbon, 45 ml of glacial acetic acid and 45 ml of methanol was hydrogenated for 3.5 hours in a Parr apparatus. The mixture was then filtered and the solvent removed, giving 6.6 g of the desired compound as a colorless oil.

EXAMPLE 22

17-([1,1'-Biphenyl]-4-yloxy)-4,7-dihydroxy-N,N,N-trimethyl-3,5,9-trioxa-4-phosphaheptadecan-1-aminium, 4-oxide, hydroxide, inner salt A mixture of 9.7 g of 17-([1,1'-biphenyl]-4-yloxy)-4-hydroxy-N,N,N-trimethyl-7-(phenylmethoxy)-3,5,9-trioxa-4-phosphaheptadecan-1-aminium, 4-oxide, hydroxide, inner salt, 0.9 g of palladium on carbon, 55 ml of glacial acetic acid and 55 ml of methanol was hydrogenated overnight in a Parr apparatus. The mixture was filtered, the solvent removed, ether was added and the solid collected, giving 7 g of the desired compound as a white solid, mp 95°-97° C.

EXAMPLE 23

7-(Acetyloxy)-4-hydroxy-N,N,N-trimethyl-3,5,9,12,15-pentaoxa-4-phosphapentacosan-1-aminium, 4-oxide, hydroxide, inner salt A mixture of 6.7 g of 4,7-dihydroxy-N,N,N-trimethyl-3,5,9,12,15-pentaoxa-4-phosphapentacosan-1-aminium, 4-oxide, hydroxide, inner salt, 35.21 g of acetic anhydride, 13.96 g of triethylamine and 400 ml of chloroform was refluxed for 4 hours. The solvent and excess anhydride were removed at reduced pressure and the residue chromatographed on 300 ml (dry volume) of silica gel, eluting first with chloroform:methanol (8:2) to remove higher Rf impurities and then eluting the product with chloroform:methanol:water (70:30:4.5). The solvents were removed, the residue was stirred with ether and then the ether was decanted from the precipitated oil. The oil was dried at reduced pressure, giving 6.46 g of the desired product as a colorless gel.

EXAMPLE 24

7-(Acetyloxy)-4-hydroxy-N,N,N-trimethyl-3,5,9,18,21,24-hexaoxa-4-phosphapentacosan-1-aminium, 4-oxide, hydroxide, inner salt A mixture of 3.5 g of 19,22-dihydroxy-N,N,N-trimethyl-2,5,8,17,21,23-hexaoxa-2-phosphapentacosan-25-aminium, oxide, hydroxide, inner salt, 18.32 g of acetic anhydride, 7.26 g of triethylamine and 200 ml of chloroform was refluxed for 4 hours. The solvent and excess anhydride were removed at reduced pressure giving 3.56 g of the desired product as an oil.

EXAMPLE 25

7-(Acetyloxy)-17-([1,1'-biphenyl]-4-yloxy)-4-hydroxy-N,N,N-trimethyl-3,5,9-trioxa-4-phosphaheptadecan-1-aminium, 4-oxide, hydroxide, inner salt A mixture of 4 g of 17-([1,1'-biphenyl]-4-yloxy)-4,7-dihydroxy-N,N,N-trimethyl-3,5,9-trioxa-4-phosphaheptadecan-1-aminium, 4-oxide, hydroxide, inner salt, 18.99 g of acetic anhydride, 7.53 g of triethylamine and 200 ml of chloroform was refluxed for 6 hours. The solvent was removed and the residue chromatographed on 200 ml (dry volume) of silica gel, eluting first with chloroform:methanol (7:3) to remove higher Rf material and then eluting the product with chloroform:methanol:water, giving, after precipitation with ether, 3.9 g of the desired product as a white solid, mp 90°–93° C.

What is claimed is:

1. A method of treating hypertension in a warm-blooded animal comprising administering to said animal an effective agmount of a compound, including the individual R and S enantiomers and racemic mixture, represented by the formula:

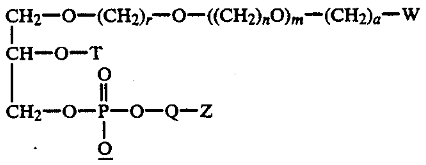

wherein W is selected from the group consisting of methyl and phenyl, alone or substituted with $C_1$–$C_3$ alkyl, $C_1$–$C_3$ alkoxy and phenyl; r, n, m and a are integers such that the expression $r+(n+1)m+a$ is also an integer and has a value of 3 to 20; r is greater than or equal to 2; n is greater than or equal to 2; m is greater than or equal to zero and a is greater than or equal to zero; T is selected from the group consisting of hydrogen and

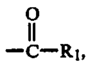

wherein $R_1$ is selected from the group consisting of hydrogen, $C_1$–$C_4$ branched or straight chain alkyl, $C_1$–$C_4$ branched or straight chain alkoxy and $C_1$–$C_4$ branched or straight chain alkylamino; Q is a bivalent radical selected from $-(CH_2)_p-$ and $-(CHR)_p-$, wherein p is an integer 2–12 and the moiety $-(CHR)_p-$ represents an alkylene chain which is substituted by one or more $C_1$–$C_{10}$ alkyl groups or phenyl groups; Z is selected from the group consisting of $\pm N(R_2)_3$ and and 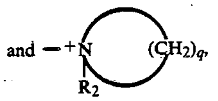

wherein $R_2$ may be the same or different and is selected from the group consisting of hydrogen and $C_1$–$C_4$ branced or straight chain alkyl and q is an integer from 4–7; in either the racemic or optically active forms.

2. A pharmaceutical composition comprising a compound including the individual R and S enantiomers and racemic mixture, represented by the formula:

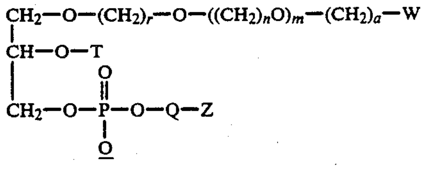

wherein W is selected from the group consisting of methyl and phenyl, alone or substituted with $C_1$–$C_3$ alkyl, $C_1$–$C_3$ alkoxy and phenyl; r, n, m and a are integers such that the expression $r+(n+1)m+a$ is also an integer and has a value of 3 to 20; r is greater than or equal to 2; n is greater than or equal to 2; m is greater than or equal to zero and a is greater than or equal to zero; T is selected from the group consisting of hydrogen and

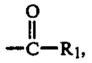

wherein $R_1$ is selected from the group consisting of hydrogen, $C_1$–$C_4$ branched or straight chain alkyl, $C_1$–$C_4$ branched or straight chain alkoxy and $C_1$–$C_4$ branched or straight chain alkylamino; Q is a bivalent radical selected from $-(CH_2)_p-$ and $-(CHR)_p-$ represents an alkylene chain which is substituted by one or more $C_1$–$C_{10}$ alkyl groups or phenyl groups; Z is selected from the group consisting of $\pm N(R_2)_3$ and and 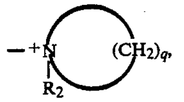

wherein $R_2$ may be the same or different and is selected from the group consisting of hydrogen and $C_1$–$C_4$ branced or straight chain alkyl and q is an integer from 4–7; in either the racemic or optically active forms, in association with a pharmaceutically acceptable carrier.

3. A method of treating hypertension in a warm-blooded animal comprising administering to said animal an effective amount of a compound, including the individual R and S enantiomers and racemic mixtures represented by the formula:

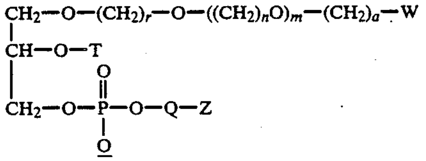

wherein W is selected from methyl and phenyl, alone, or substituted with phenyl; r, n, m and a are integers such that the expression r+(n+1)m+a is also an integer and has a value of 3 to 20; r is from 2 to 8; n is 2; m is from zero to 2 and a is from zero to 9; T is selected from hydrogen and

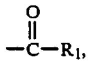

wherein $R_1$ is selected from hydrogen and $C_1$-$C_4$ alkyl; Q is a bivalent radical selected from —$(CH_2)_p$— wherein p is an integer from 2 to 5 and —$CHR)_p$— wherein p is an integer of 2 to 5 and R is methyl or phenyl; and Z is selected from $\pm N(R_2)_3$ and

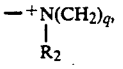

wherein $R_2$ may be the same or different and is selected from the group consisting of hydrogen and $C_1$-$C_4$ alkyl and q is an integer from 4 to 7.

4. A pharmaceutical composition comprising a compound including the individual R and S enantiomers and racemic mixture in association with a pharmaceutically acceptable carrier, wherein said compound is

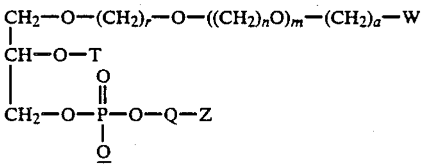

wherein W is selected from methyl and phenyl, alone, or substituted with phenyl; r, n, m and a are integers such that the expression r+(n+1)m+a is also an integer and has a value of 3 to 20; r is from 2 to 8; n is 2; m is from zero to 2 and a is from zero to 9; T is selected from hydrogen and

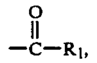

wherein $R_1$, is selected from hydrogen and $C_1$-$C_4$ alkyl; Q is a bivalent radical selected from —$(CH_2)_p$— wherein p is an integer from 2 to 5 and —$CHR)_p$— wherein p is an integer of 2 to 5 and —$(CHR)_q$, wherein p is an integer from 2 to 5 and R is methyl or phenyl; and Z is selected from $\pm N(R_2)_3$ and

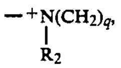

wherein $R_2$ may be the same or different and is selected from the group consisting of hydrogent and $C_1$-$C_4$ alkyl and q is an integer from 4 to 7.

5. Compounds, including the individual R and S enantiomers and the racemic mixtures represented by the formula:

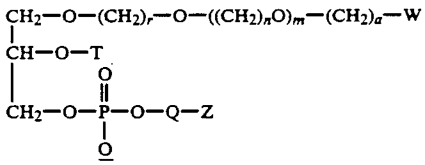

wherein W is selected from the group consisting of methyl and phenyl, alone, or substituted with $C_1$-$C_3$ alkyl, $C_1$-$C_3$ alkoxy and phenyl; r, n, m and a are integers such that the expression r+(n+1)m+a is also an integer and has a value of 3 to 20; r is greater than or equal to 2; n is greater than or equal to 2; m is greater than or equal to zero and a is greater than or equal to zero; T is selected from the group consisting of hydrogen and

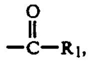

wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino; Q is a bivalent radical selected from —$(CH_2)_p$— and —$(CHR)_p$—, wherein p is an integer 2-12 and the moiety —$(CHR)_p$— represents an alkylene chain which is substituted by one or more $C_1$-$C_{10}$ alkyl groups or phenyl groups; Z is selected from the group consisting of $\pm N(R_2)_3$ and and 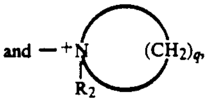

wherein $R_2$ may be the same or different and is selected from the group consisting of hydrogen and $C_1$-$C_4$ branced or straight chain alkyl and q is an integer from 4-7; in either the racemic or optically active forms.

6. The compounds according to claim 5 wherein T is

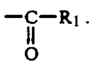

7. The compounds according to claim 6 wherein Z is —$N(CH_3)_3$.

8. The compounds according to claim 7 wherein Q is —$(CH_2)_p$—.

9. The compounds according to claim 8 wherein T is

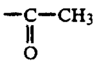

and p is 2.

10. The compounds according to claim 9 wherein W is methyl.

11. The compounds according to claim 9 wherein W is a phenyl group, alone, or substituted with $C_1$-$C_3$ alkyl, $C_1$—$C_3$ alkoxy, and phenyl.

12. The compounds according to claim 10 wherein m is zero.

13. The compounds according to claim 11 wherein m is zero.

14. Compounds, including the individual R and S enantiomers and the racemic mixtures represented by the formula:

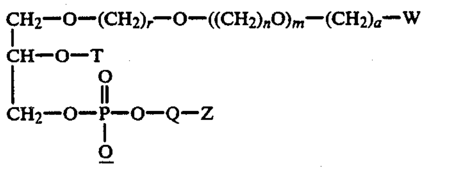

wherein W is selected from methyl and phenyl, alone, or substituted with phenyl; r, n m and a are integers such that the expression $r+(n+1)m+a$ is also an integer and has a value of 3 to 20; r is from 2 to 8; n is 2; m is from zero to 2 and a is from zero to 9; T is selected from hydrogen and

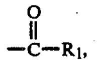

wherein $R_1$ is selected from hydrogen and $C_1$-$C_4$ alkyl; Q is a bivalent radical selected from $-(CH_2)_p-$, wherein p is an integer 2 to 5 and $-(CHR)_p-$, wherein p is an integer 2 to 5 and R is methyl or phenyl and Z is selected from $\pm N(R_2)_3$ and

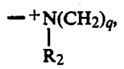

wherein $R_2$ may be the same or different and is selected from hydrogen and $C_1$-$C_4$ alkyl and q is an integer from 4 to 7.

* * * * *